(12) United States Patent
Pappady (10) Patent No.: US 10,285,841 B2
(45) Date of Patent: May 14, 2019

(54) STABILIZING AND MOBILITY-ENHANCING BRACE FOR THE SHOULDER JOINT

(71) Applicant: Rojan John Pappady, Queens Village, NY (US)

(72) Inventor: Rojan John Pappady, Queens Village, NY (US)

(*) Notice: Subject to any disclaimer, the term of this patent is extended or adjusted under 35 U.S.C. 154(b) by 441 days.

(21) Appl. No.: 15/256,358

(22) Filed: Sep. 2, 2016

(65) Prior Publication Data

US 2017/0065450 A1    Mar. 9, 2017

Related U.S. Application Data

(60) Provisional application No. 62/214,783, filed on Sep. 4, 2015.

(51) Int. Cl.
*A61F 5/00* (2006.01)
*A61F 5/01* (2006.01)
*A61F 5/37* (2006.01)

(52) U.S. Cl.
CPC .......... *A61F 5/0118* (2013.01); *A61F 5/3723* (2013.01)

(58) Field of Classification Search
USPC ..................................... 602/4, 20
See application file for complete search history.

(56) References Cited

U.S. PATENT DOCUMENTS

| | | | | | |
|---|---|---|---|---|---|
| 4,559,932 | A | * | 12/1985 | Salort | A61F 5/0118 602/20 |
| 5,383,844 | A | * | 1/1995 | Munoz | A61F 5/013 602/20 |
| 6,099,489 | A | * | 8/2000 | Herzberg | A61F 13/10 128/876 |
| 6,152,891 | A | * | 11/2000 | Carlson | A61F 5/0118 602/20 |
| 6,306,111 | B1 | * | 10/2001 | Dean | A61F 5/3753 128/DIG. 19 |
| 6,979,303 | B2 | * | 12/2005 | Jestrabek-Hart | A61F 5/3738 2/45 |
| 7,052,478 | B1 | * | 5/2006 | Bodenschatz | A61F 5/3738 128/878 |
| 7,320,669 | B2 | * | 1/2008 | Campbell | A61F 5/3723 602/4 |
| 8,591,441 | B2 | * | 11/2013 | Bonutti | A61F 5/013 602/16 |
| 8,992,451 | B2 | * | 3/2015 | Fout | A61F 5/3753 128/869 |

(Continued)

*Primary Examiner* — Kim M Lewis (57) ABSTRACT

A stabilizing and mobility-enhancing brace for the shoulder joint is a device for providing structural support to the user's shoulder joint while allowing a degree of mobility for the user's shoulder and the user's arm. The device includes a shoulder joint brace for providing stability to the shoulder as well as an elbow brace for providing stability to the arm. The elbow brace is connected to the shoulder joint brace through a mobility strap and a deltoid connector strap that enable movement of the user's arm. The mobility strap is engaged through a strap groove on the shoulder joint brace and is able to slide over a roller assembly within the strap groove. The shoulder joint brace is also secured to a lateral thoracic brace worn on the user's body via a torso strap assembly. The elbow brace is fastened in place via a plurality of elbow securing straps.

14 Claims, 6 Drawing Sheets

(56) References Cited

U.S. PATENT DOCUMENTS

| | | | |
|---|---|---|---|
| 2003/0208146 A1* | 11/2003 | Kania | A61F 5/0118 602/19 |
| 2005/0119596 A1* | 6/2005 | Kania | A61F 5/0118 602/20 |
| 2006/0129078 A1* | 6/2006 | Ledergerber | A61F 5/373 602/20 |
| 2007/0106187 A1* | 5/2007 | Campbell | A61F 5/3723 602/19 |
| 2009/0149787 A1* | 6/2009 | Scott | A61F 5/3723 602/4 |
| 2010/0210985 A1* | 8/2010 | Kuorak | A61F 5/3723 602/20 |
| 2011/0021962 A1* | 1/2011 | Sorrenti | A61F 5/3753 602/20 |
| 2011/0034841 A1* | 2/2011 | Richard | A61F 5/3746 602/4 |
| 2012/0101419 A1* | 4/2012 | Bonutti | A61F 5/013 602/20 |
| 2012/0101421 A1* | 4/2012 | Albrecht | A61F 5/013 602/20 |
| 2013/0085433 A1* | 4/2013 | Grant | A61F 5/013 602/16 |
| 2013/0092179 A1* | 4/2013 | Reinhardt | A61F 5/3723 128/878 |
| 2013/0184627 A1* | 7/2013 | Vedder | A61B 17/1739 602/20 |
| 2013/0237893 A1* | 9/2013 | Knox | A61F 5/0118 602/20 |
| 2014/0171846 A1* | 6/2014 | Bonutti | A61F 5/013 602/20 |
| 2015/0351951 A1* | 12/2015 | Fair | A61F 5/3753 602/20 |

* cited by examiner

STABILIZING AND MOBILITY-ENHANCING BRACE FOR THE SHOULDER JOINT

The current application claims a priority to the U.S. Provisional Patent application Ser. No. 62/214,783 filed on Sep. 4, 2015.

FIELD OF THE INVENTION

The present invention relates generally to a medical brace. More specifically, the present invention is a stabilizing and mobility-enhancing brace for the shoulder joint that addresses physical complications associated with post-stroke systems. The present invention also provides structural support to minimize unwanted movements that may trigger abnormal synergy patterns in the upper extremities and shoulder joint.

BACKGROUND OF THE INVENTION

Shoulder mobility dysfunction is a very common condition that may be caused by a variety of medical conditions or trauma. In the early periods following the onset of a stroke, the hemiplegic arm appears weak and does not have the strength and tone to maintain normal joint structure and integrity. The shoulder musculature becomes weak, particularly the rotator cuff muscle. This results in the rotator cuff muscle being unable to maintain the humeral head in the glenoid fossa, increasing the risk of shoulder subluxation. The increased pull of the affected extremity in the downward direction may increase the pull on the shoulder joint capsule and associated structures, eventually resulting in shoulder subluxation. In addition, mechanical overstretching of the weakened supraspinatus and the weakened deltoid muscle increases the risk of soft tissue injury and pain. The present invention seeks to address these issues relating to shoulder mobility dysfunction.

The present invention is a stabilizing and mobility-enhancing brace for the shoulder joint. The present invention is utilized to provide structural support to the user's shoulder joint while allowing a degree of mobility for the user's shoulder and the user's arm. In its preferred embodiment, the present invention is primarily intended for use with stroke victims in the early periods following a stroke.

DETAIL DESCRIPTIONS OF THE INVENTION

All illustrations of the drawings are for the purpose of describing selected versions of the present invention and are not intended to limit the scope of the present invention.

The present invention is a stabilizing and mobility-enhancing brace for the shoulder joint. The present invention is shown in FIGS. 1-6 and comprises a shoulder joint brace 1, an elbow brace 4, a mobility strap 7, a strap groove 8, a plurality of elbow securing straps 9, a lateral thoracic brace 13, a torso strap assembly 18, and a roller assembly 23.

The shoulder joint brace 1 serves to provide structural support and stability to the shoulder joint while still allowing a degree of mobility. The elbow brace 4 provides similar structural support, stability, and mobility to the user's arm. The mobility strap 7 is utilized to connect the shoulder joint brace 1 to the elbow brace 4 and additionally facilitates mobility of the user's arm. The strap groove 8 is an opening within the shoulder joint brace 1 through which the mobility strap 7 is able to move to provide mobility to the user's arm. The strap groove 8 traverses through the shoulder joint brace 1 from an anterior portion 2 of the shoulder joint brace 1 to a posterior portion 3 of the shoulder joint brace 1. The strap groove 8 thus forms an opening within the shoulder joint brace 1 through which the mobility strap 7 is able to move. The mobility strap 7 is slidably positioned through the strap groove 8 and is able to slide within the strap groove 8 based on movement of the user's arm. The mobility strap 7 is terminally connected to an anterior section 5 of the elbow brace 4 and a posterior section 6 of the elbow brace 4. Because the elbow brace 4 is worn on the user's elbow region, movement of the user's arm causes the mobility strap 7 to slide within the strap groove 8, facilitating mobility of the user's arm.

The plurality of elbow securing straps 9 is utilized to ensure that the elbow brace 4 remains fastened to the user's elbow during use of the present invention. The anterior section 5 is connected to the posterior section 6 by the plurality of elbow securing straps 9. The anterior section 5 and the posterior section 6 may thus be tightened or loosened around the user's elbow by tightening or loosening the plurality of elbow securing straps 9. Additionally, the plurality of elbow securing straps 9 is positioned in between the anterior section 5 and the posterior section 6, allowing the plurality of elbow securing straps 9 to connect the anterior section 5 to the posterior section 6 and additionally enabling the plurality of elbow securing straps 9 to be tightened or loosened as needed.

The lateral thoracic brace 13 and the torso strap assembly 18 are utilized to secure the present invention to the user's body. The lateral thoracic brace 13 is worn around the user's lateral thoracic region opposite to the side of the user's body on which the shoulder joint brace 1 is worn. The torso strap assembly 18 is utilized to secure the shoulder joint brace 1 to the lateral thoracic brace 13 and is worn across the user's torso. The shoulder joint brace 1 is connected to the lateral thoracic brace 13 through the torso strap assembly 18, enabling the torso strap assembly 18 to be adjusted to tighten or loosen the present invention around the user's torso.

Figure 6:
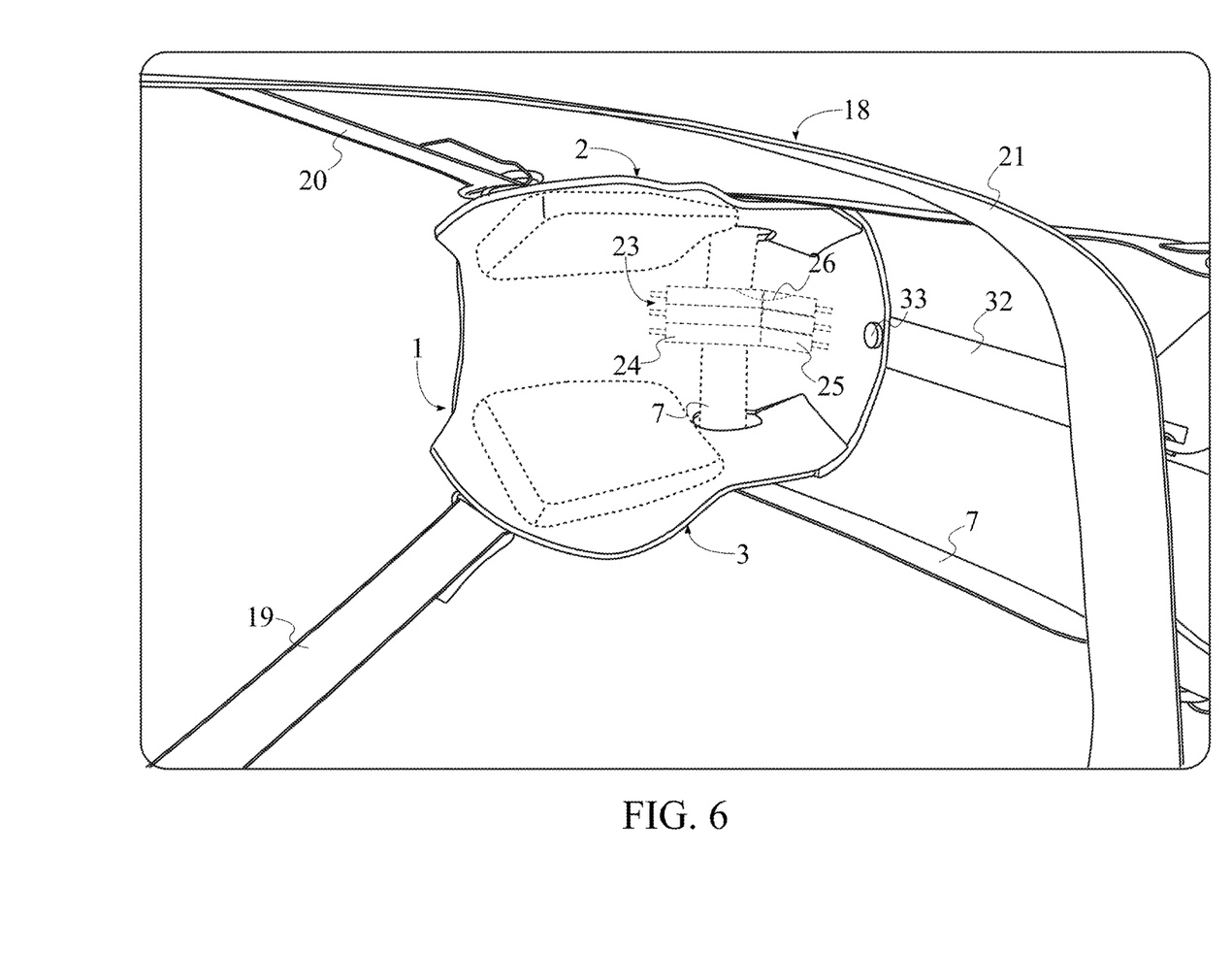
FIG. 6 is a detail view of the roller assembly within the shoulder joint brace.

With reference to FIG. 6, the roller assembly 23 facilitates movement of the mobility strap 7 through the strap groove 8. The roller assembly 23 is rotatably positioned within the strap groove 8, enabling the mobility strap 7 to be placed into contact with the roller assembly 23 within the strap groove 8. The mobility strap 7 is trained about the roller assembly 23. As a result, the roller assembly 23 is able to rotate as the mobility strap 7 slides within the strap groove 8.

Figure 2:
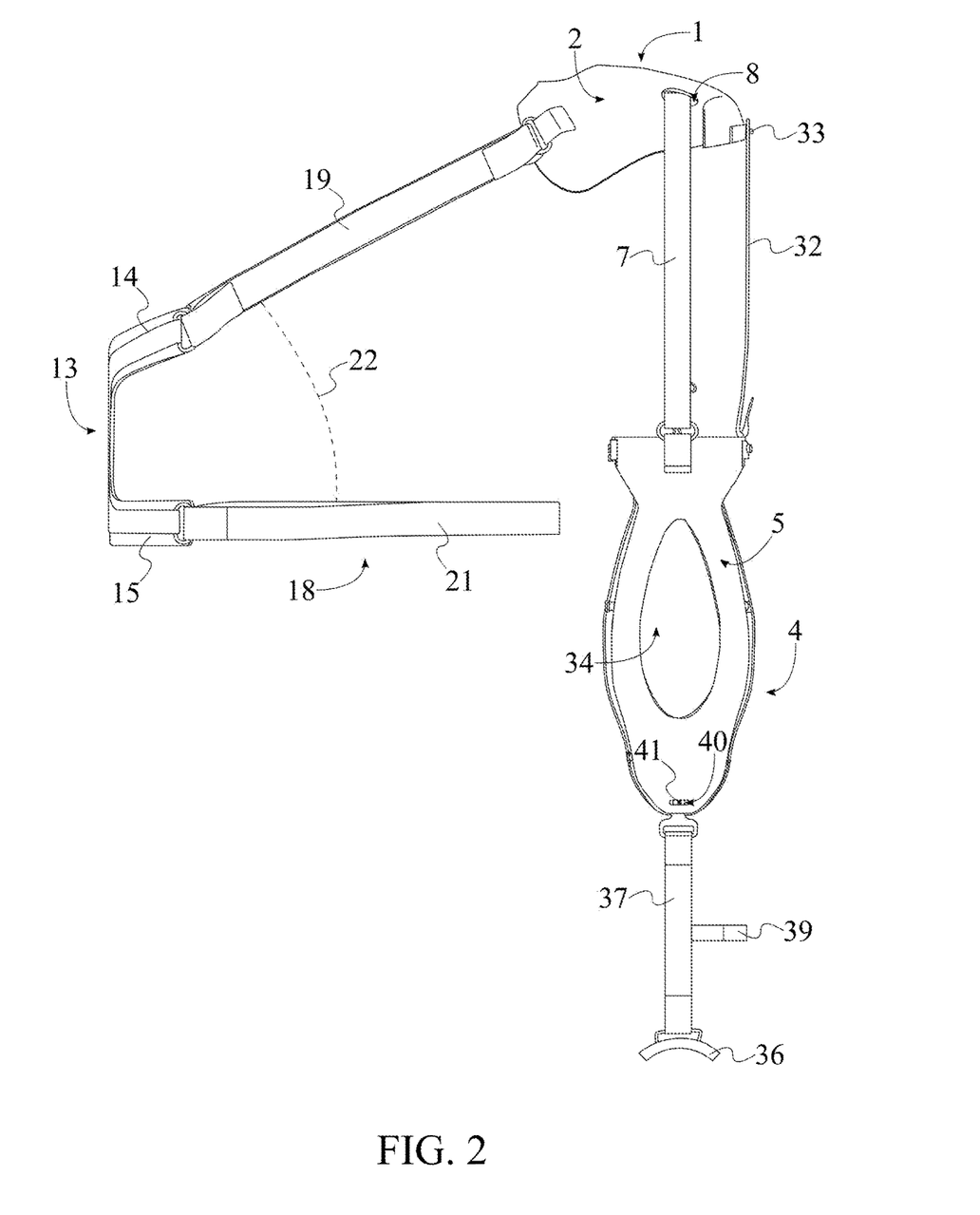
FIG. 2 is a front view of the present invention.
Figure 3:
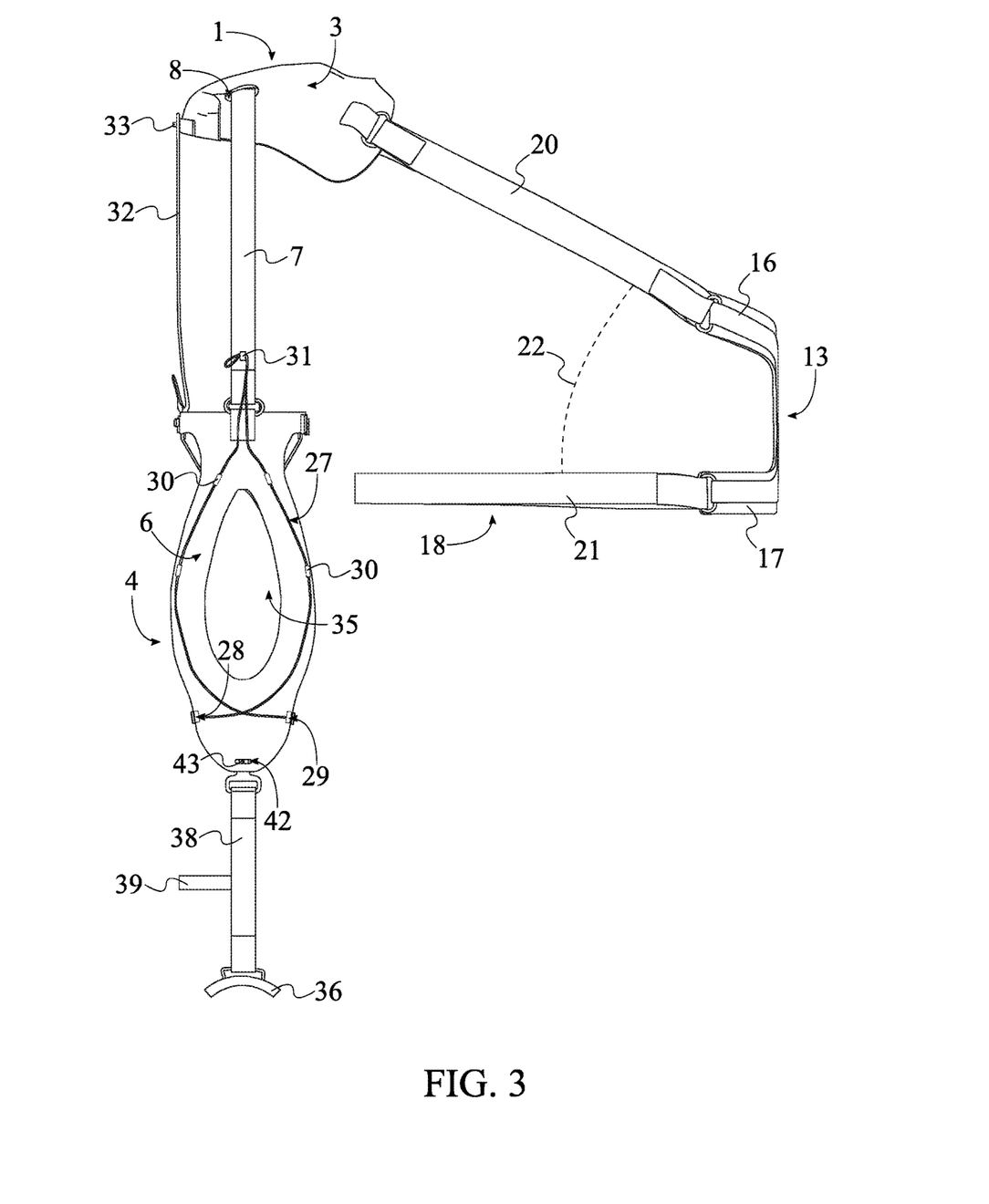
FIG. 3 is a rear view of the present invention.

The torso strap assembly 18 comprises an anterior stabilizing strap 19, a posterior stabilizing strap 20, and a circumferential stabilizing strap 21. The anterior stabilizing strap 19 and the posterior stabilizing strap 20 are positioned on the anterior and the posterior of the user's body, respectively. The circumferential stabilizing strap 21 is wrapped around the user's torso and provides further security for the present invention on the user's body. The lateral thoracic brace 13 comprises a first anterior wing 14, a second anterior wing 15, a first posterior wing 16, and a second posterior wing 17. The first anterior wing 14, the second anterior wing 15, the first posterior wing 16, and the second posterior wing 17 serve as mounting points on the lateral thoracic brace 13 for the anterior stabilizing strap 19, the posterior stabilizing strap 20, and the circumferential stabilizing strap 21. The anterior stabilizing strap 19 is connected from the anterior portion 2 to the first anterior wing 14. As a result, the anterior stabilizing strap 19 connects the shoulder joint brace 1 to the lateral thoracic brace 13 on the anterior of the user's body. The posterior stabilizing strap 20 is connected from the posterior portion 3 to the first posterior wing 16, enabling the posterior stabilizing strap 20 to connect the shoulder joint brace 1 to the lateral thoracic brace 13 on the posterior of the user's body. The circumferential stabilizing strap 21 is connected from the second anterior wing 15 to the second posterior wing 17. As a result, the circumferential stabilizing strap 21 is wrapped around the user's body and is secured in two positions on the lateral thoracic brace 13. The first anterior wing 14 and the first posterior wing 16 are positioned superior to the second anterior wing 15 and the second posterior wing 17, positioning the anterior stabilizing strap 19 and the posterior stabilizing strap 20 superior to the circumferential stabilizing strap 21 on the user's body. With reference to FIG. 2 and FIG. 3, in the preferred embodiment of the present invention, the anterior stabilizing strap 19 is oriented at an acute angle 22 relative to the circumferential stabilizing strap 21. Similarly, the posterior stabilizing strap 20 is oriented at an acute angle 22 relative to the circumferential stabilizing strap 21. The anterior stabilizing strap 19 and the posterior stabilizing strap 20 thus function as cross straps on the user's body.

With reference to FIG. 6, in the preferred embodiment of the present invention, the roller assembly 23 comprises at least one elongated roller 24 and at least one oblique roller 25. The at least one oblique roller 25 is terminally connected to the at least one elongated roller 24. The at least one oblique roller 25 is thus positioned and oriented to accommodate the natural contour of the user's shoulder. The at least one oblique roller 25 is oriented at an obtuse angle 26 relative to the at least one elongated roller 24 to accommodate the curved portion of the user's shoulder.

The plurality of elbow securing straps 9 comprises a first securing strap 10, a second securing strap 11, and a third securing strap 12. The first securing strap 10 is positioned adjacent to the mobility strap 7 and is thus positioned in between the user's shoulder and the user's elbow. The first securing strap 10 and the third securing strap 12 are positioned opposite to each other across the anterior section 5 and the posterior section 6. The third securing strap 12 is thus positioned in between the user's wrist and the user's elbow. The second securing strap 11 is positioned in between the first securing strap 10 and the third securing strap 12 and in the preferred embodiment of the present invention, is positioned on the user's elbow.

With reference to FIG. 3, the present invention further comprises a tightening cord 27, a plurality of guide loops 30, and a cord cinch 31. The tightening cord 27 is utilized to tighten and loosen the elbow brace 4. The plurality of guide loops 30 serves to secure the tightening cord 27 in place on the elbow brace 4. The cord cinch 31 is utilized to maintain the tightness of the elbow brace 4 through the tightening cord 27 by preventing the tightening cord 27 from slackening. The plurality of guide loops 30 is positioned about the posterior section 6, allowing the tightening cord 27 to be positioned about the posterior section 6. A first end 28 of the tightening cord 27 is fixed to the third securing strap 12 while a second end 29 of the tightening cord 27 is fixed to the third securing strap 12, adjacent to the first end 28. The third securing strap 12 may thus be tightened and loosened via the tightening cord 27. The tightening cord 27 traverses through the plurality of guide loops 30, enabling the tightening cord 27 to be retained within the plurality of guide loops 30. The cord cinch 31 is tensionably engaged with the tightening cord 27, enabling the cord cinch 31 to maintain the tension in the tightening cord 27 after a desired tightness of the elbow brace 4 has been achieved. The cord cinch 31 is positioned adjacent to the first securing strap 10 and is thus offset from the third securing strap 12, enabling the tightening cord 27 to be pulled in order to tighten the third securing strap 12.

The present invention further comprises a deltoid connector strap 32 and a fulcrum 33. Similar to the mobility strap 7, the deltoid connector strap 32 is utilized to facilitate the mobility of the user's arm when the present invention is worn. The fulcrum 33 is the mounting point for the deltoid connector strap 32. The fulcrum 33 is positioned on the shoulder joint brace 1, opposite to the torso strap assembly 18, enabling the deltoid connector strap 32 to be mounted to the shoulder joint brace 1. The deltoid connector strap 32 is terminally connected to the fulcrum 33 and the first securing strap 10. As a result, the deltoid connector strap 32 serves as a tether between the shoulder joint brace 1 and the first securing strap 10. The deltoid connector strap 32 is pivotally connected to the fulcrum 33, allowing the deltoid connector strap 32 to pivot about the fulcrum 33 when the user's arm is moved, improving the user's arm mobility.

The present invention further comprises an anterior opening 34 and a posterior opening 35. The anterior opening 34 traverses centrally through the anterior section 5 while the posterior opening 35 traverses centrally through the posterior section 6. The anterior opening 34 and the posterior opening 35 thus facilitate user arm mobility by allowing the elbow brace 4 to flex and otherwise adjust based on the user's arm movement.

Figure 1:
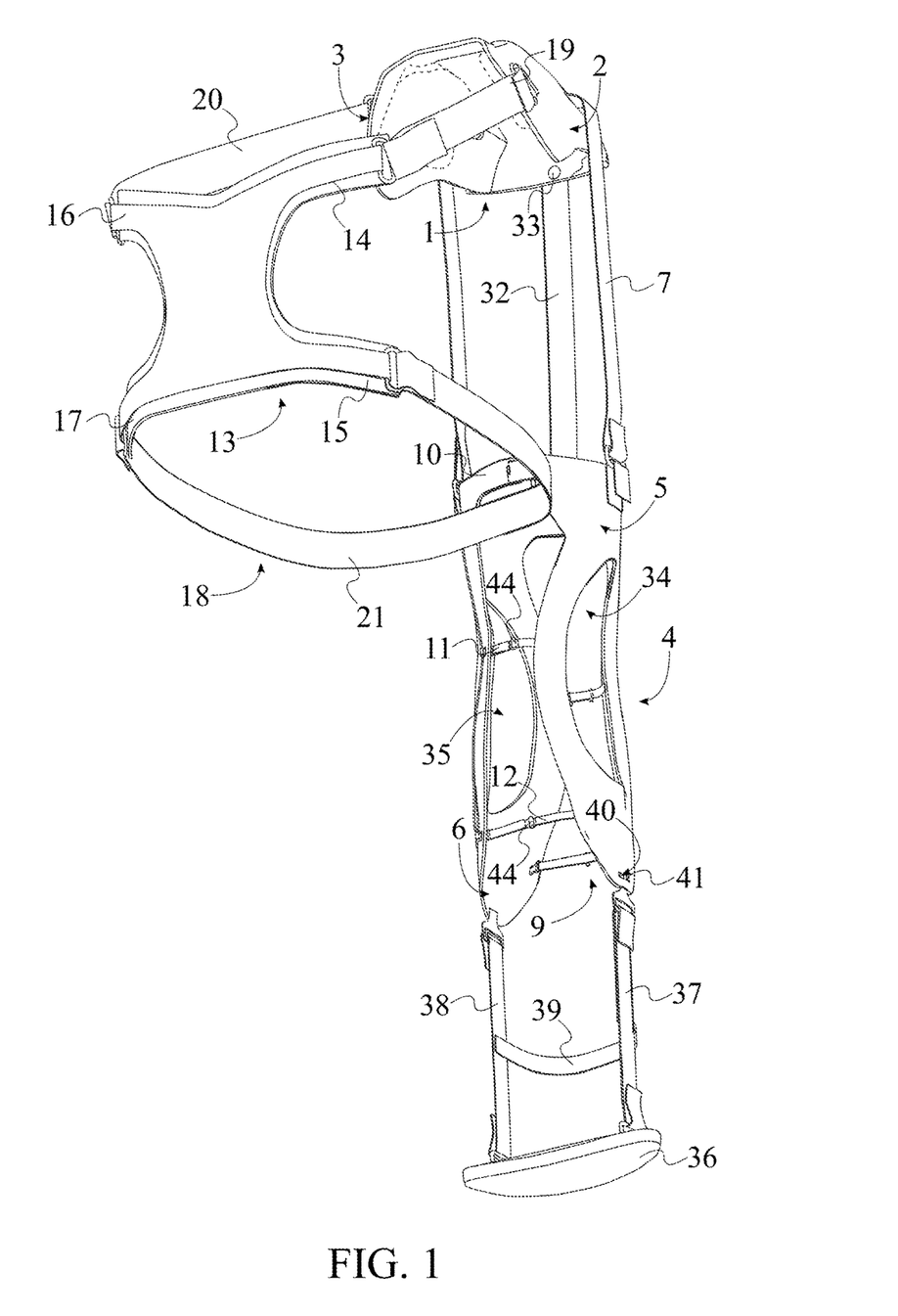
FIG. 1 is a perspective view of the present invention.
Figure 4:
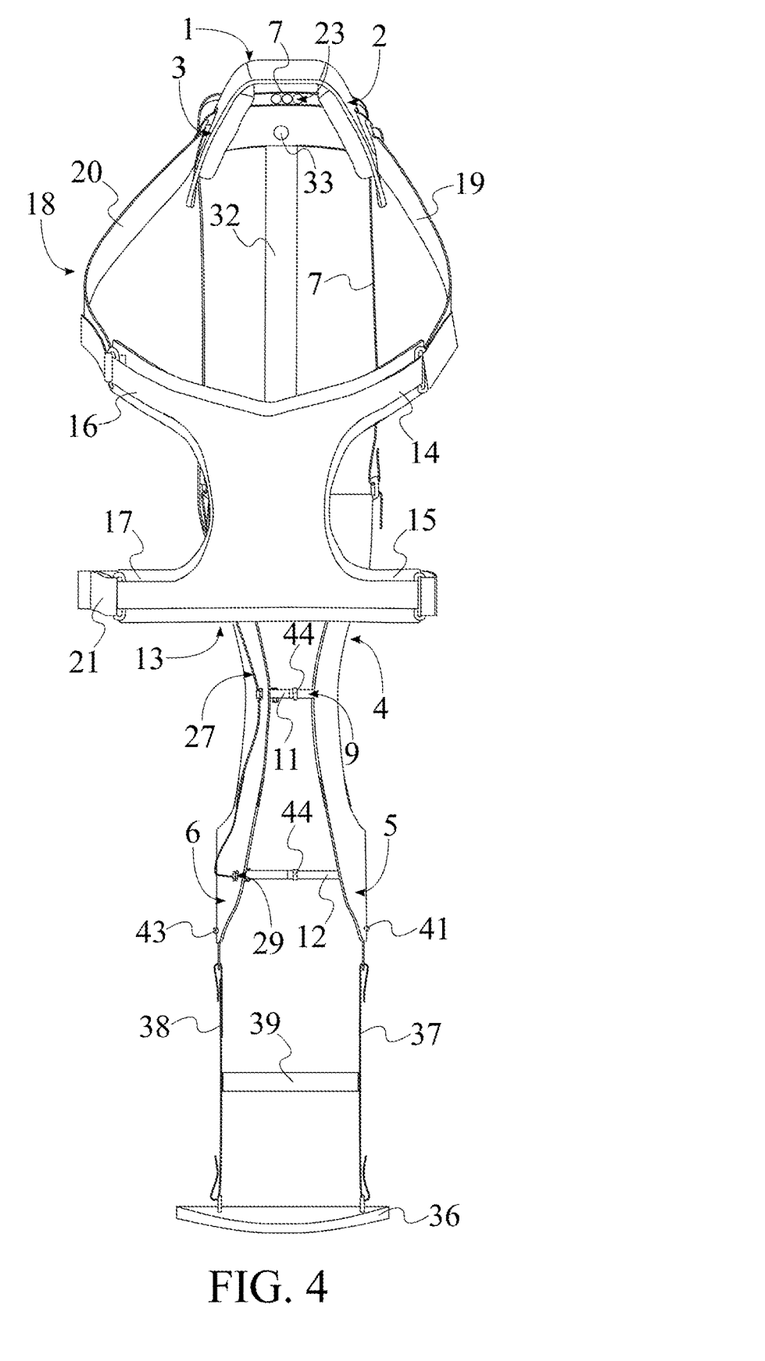
FIG. 4 is a right side view of the present invention.
Figure 5:
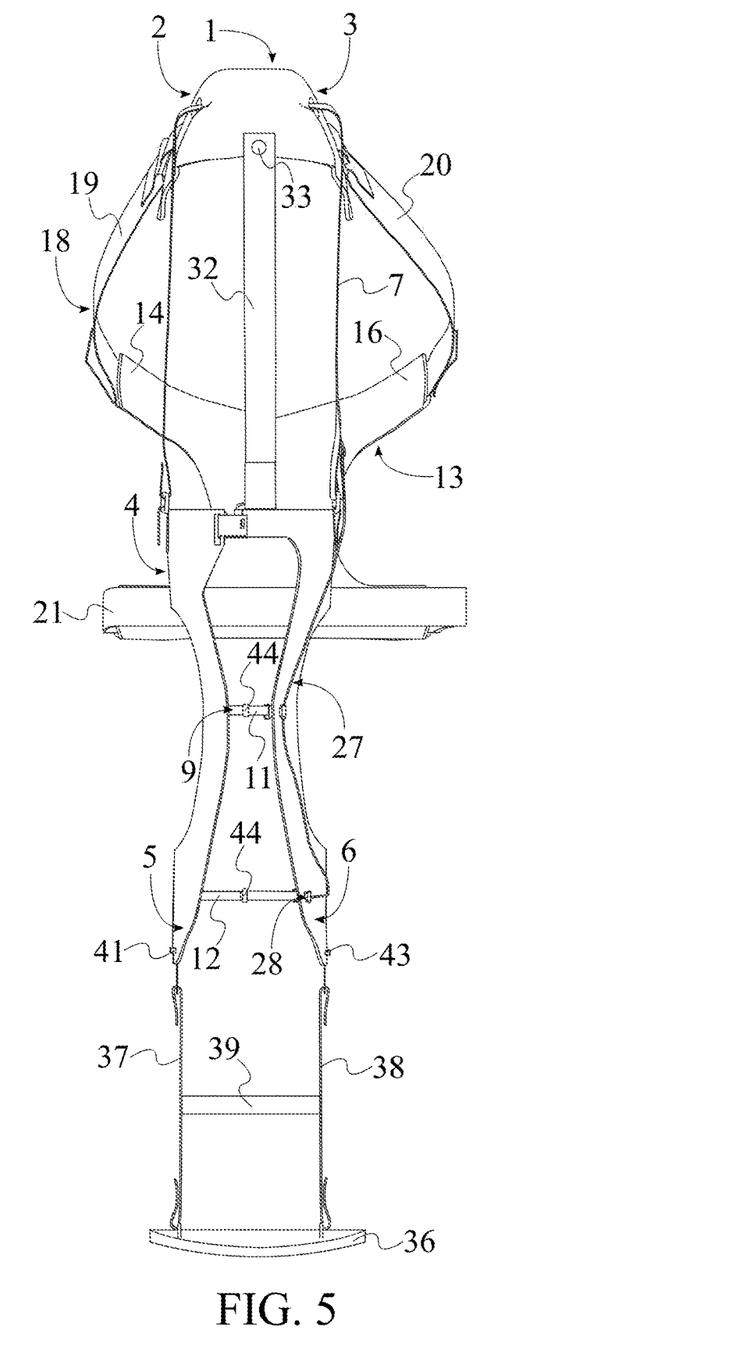
FIG. 5 is a left side view of the present invention.

With reference to FIG. 1, FIG. 4, and FIG. 5, the present invention further comprises a hand brace 36, a first forearm strap 37, and a second forearm strap 38. The hand brace 36 provides stability to the user's hand and forearm during use of the present invention. The first forearm strap 37 and the second forearm strap 38 are utilized to connect the elbow brace 4 to the hand brace 36. The first forearm strap 37 is terminally connected to the anterior section 5 and the hand brace 36 while the second forearm strap 38 is terminally connected to the posterior section 6 and the hand brace 36. The hand brace 36 is thus tethered to the elbow brace 4 by the first forearm strap 37 and the second forearm strap 38. The present invention further comprises a wrist positioning strap 39. The wrist positioning strap 39 provides additional support for the user's arm. The wrist positioning strap 39 is terminally connected to the first forearm strap 37 and the second forearm strap 38 and is adjustable to enable the first forearm strap 37 and the second forearm strap 38 to be drawn closer together or separated.

The present invention further comprises a first slot 40, a first pin 41, a second slot 42, and a second pin 43. The first slot 40 and the second slot 42 serve as tracks for the first pin 41 and the second pin 43, enabling adjustment of the first forearm strap 37 and the second forearm strap 38. The first slot 40 traverses into the anterior section 5, opposite to the mobility strap 7, forming an opening on the anterior section 5. Similarly, the second slot 42 traverses into the posterior slot, opposite to the mobility strap 7, forming an opening on the posterior section 6. The first pin 41 is terminally connected to the first forearm strap 37, opposite to the hand brace 36, while the second pin 43 is terminally connected to the second forearm strap 38, opposite to the hand brace 36. The first forearm strap 37 and the second forearm strap 38 may thus be adjusted based on the user's movement. The first pin 41 is slidably engaged into the first slot 40 while the second pin 43 is slidably engaged into the second slot 42. As a result, the first pin 41 may slide within the first slot 40 and the second pin 43 may slide within the second slot 42 based on the user's arm movements and the movement of the first forearm strap 37 and the second forearm strap 38.

The present invention further comprises a plurality of strap retainers 44. The plurality of strap retainers 44 is utilized to prevent the plurality of elbow securing straps 9 from unraveling or separating. Each of the plurality of strap retainers 44 is positioned on a corresponding strap from the plurality of elbow securing straps 9, providing retention for each of the plurality of elbow securing straps 9.

Although the present invention has been explained in relation to its preferred embodiment, it is understood that many other possible modifications and variations can be made without departing from the spirit and scope of the present invention as hereinafter claimed.

What is claimed is:

1. A stabilizing and mobility-enhancing brace for a shoulder joint comprising:
   a shoulder joint brace;
   an elbow brace;
   a mobility strap;
   a strap groove;
   a plurality of elbow securing straps;
   a lateral thoracic brace;
   a torso strap assembly;
   a roller assembly;
   the strap groove traversing through the shoulder joint brace from an anterior portion of the shoulder joint brace to a posterior portion of the shoulder joint brace;
   the mobility strap being slidably positioned through the strap groove;
   the mobility strap being terminally connected to an anterior section of the elbow brace and a posterior section of the elbow brace;
   the anterior section being connected to the posterior section by the plurality of elbow securing straps;
   the plurality of elbow securing straps being positioned in between the anterior section and the posterior section;
   the shoulder joint brace being connected to the lateral thoracic brace through the torso strap assembly;
   the roller assembly being rotatably positioned within the strap groove; and the mobility strap being trained about the roller assembly.

2. The stabilizing and mobility-enhancing brace for the shoulder joint as claimed in claim 1 wherein,
   the torso strap assembly comprises an anterior stabilizing strap, a posterior stabilizing strap, and a circumferential stabilizing strap;
   the lateral thoracic brace comprises a first anterior wing, a second anterior wing, a first posterior wing, and a second posterior wing;
   the anterior stabilizing strap being connected from the anterior portion to the first anterior wing;
   the posterior stabilizing strap being connected from the posterior portion to the first posterior wing; and
   the circumferential stabilizing strap being connected from the second anterior wing to the second posterior wing.

3. The stabilizing and mobility-enhancing brace for the shoulder joint as claimed in claim 2 wherein,
   the first anterior wing and the first posterior wing being positioned superior to the second anterior wing and the second posterior wing.

4. The stabilizing and mobility-enhancing brace for the shoulder joint as claimed in claim 2 wherein,
   the anterior stabilizing strap being oriented at an acute angle relative to the circumferential stabilizing strap; and
   the posterior stabilizing strap being oriented at an acute angle relative to the circumferential stabilizing strap.

5. The stabilizing and mobility-enhancing brace for the shoulder joint as claimed in claim 1 wherein,
   the roller assembly comprises at least one elongated roller and at least one oblique roller;
   the at least one oblique roller being terminally connected to the at least one elongated roller; and
   the at least one oblique roller being oriented at an obtuse angle relative to the at least one elongated roller.

6. The stabilizing and mobility-enhancing brace for the shoulder joint as claimed in claim 1 wherein
   the plurality of elbow securing straps comprises a first securing strap, a second securing strap, and a third securing strap;
   the first securing strap being positioned adjacent to the mobility strap;
   the first securing strap and the third securing strap being positioned opposite to each other across the anterior section and the posterior section; and
   the second securing strap being positioned in between the first securing strap and the third securing strap.

7. The stabilizing and mobility-enhancing brace for the shoulder joint as claimed in claim 6 further comprises:
   a tightening cord;
   a plurality of guide loops;
   a cord cinch;
   the plurality of guide loops being positioned about the posterior section;
   a first end of the tightening cord being fixed to the third securing strap;
   a second end of the tightening cord being fixed to the third securing strap, adjacent to the first end;
   the tightening cord traversing through the plurality of guide loops;
   the cord cinch being tensionably engaged with the tightening cord; and
   the cord cinch being positioned adjacent to the first securing strap.

8. The stabilizing and mobility-enhancing brace for the shoulder joint as claimed in claim 1 further comprises:
   a deltoid connector strap;
   a fulcrum;
   the plurality of elbow securing straps comprises a first securing strap;
   the fulcrum being positioned on the shoulder joint brace, opposite to the torso strap assembly;
   the deltoid connector strap being terminally connected to the fulcrum and the first securing strap; and
   the deltoid connector strap being pivotally connected to the fulcrum.

9. The stabilizing and mobility-enhancing brace for the shoulder joint as claimed in claim 1 further comprises:
   an anterior opening;
   a posterior opening;
   the anterior opening traversing centrally through the anterior section of the elbow brace; and
   the posterior opening traversing centrally through the posterior section of the elbow brace.

10. The stabilizing and mobility-enhancing brace for the shoulder joint as claimed in claim 1 further comprises:
a hand brace;
a first forearm strap;
a second forearm strap;
the first forearm strap being terminally connected to the anterior section of the elbow brace and the hand brace; and
the second forearm strap being terminally connected to the posterior section of the elbow brace and the hand brace.

11. The stabilizing and mobility-enhancing brace for the shoulder joint as claimed in claim 10 further comprises:
a wrist positioning strap; and
the wrist positioning strap being terminally connected to the first forearm strap and the second forearm strap.

12. The stabilizing and mobility-enhancing brace for the shoulder joint as claimed in claim 10 further comprises:
a first slot;
a first pin;
the first slot traversing into the anterior section of the elbow brace, opposite to the mobility strap;
the first pin being terminally connected to the first forearm strap, opposite to the hand brace; and
the first pin being slidably engaged into the first slot.

13. The stabilizing and mobility-enhancing brace for the shoulder joint as claimed in claim 10 further comprises:
a second slot;
a second pin;
the second slot traversing into the posterior section of the elbow brace, opposite to the mobility strap;
the second pin being terminally connected to the second forearm strap, opposite to the hand brace; and
the second pin being slidably engaged into the second slot.

14. The stabilizing and mobility-enhancing brace for the shoulder joint as claimed in claim 1 further comprises:
a plurality of strap retainers; and
each of the plurality of strap retainers being positioned on a corresponding strap from the plurality of elbow securing straps.

* * * * *